(12) United States Patent
Zhang et al.

(10) Patent No.: US 12,733,968 B2
(45) Date of Patent: Sep. 15, 2026

(54) COMBINATION PROBE FOR CRYOABLATION AND THERMAL ABLATION WITH EXTERNAL HEATER

(71) Applicant: Varian Medical Systems, Inc., Palo Alto, CA (US)

(72) Inventors: Hongxuan Zhang, Austin, TX (US); Ryan Medema, Georgetown, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 620 days.

(21) Appl. No.: 18/186,613

(22) Filed: Mar. 20, 2023

(65) Prior Publication Data

US 2024/0315751 A1 Sep. 26, 2024

(51) Int. Cl.
*A61B 18/02* (2006.01)
*A61B 18/00* (2006.01)

(52) U.S. Cl.
CPC .... *A61B 18/02* (2013.01); *A61B 2018/00041* (2013.01); *A61B 2018/00095* (2013.01); *A61B 2018/00577* (2013.01); *A61B 2018/00791* (2013.01); *A61B 2018/00875* (2013.01); *A61B 2018/0262* (2013.01)

(58) Field of Classification Search
CPC ......... A61B 18/02; A61B 18/04; A61B 18/08; A61B 18/082; A61B 2018/00041; A61B 2018/00095; A61B 2018/0262; A61B 2018/00023; A61B 2018/0293; A61B 2018/00577; A61B 2018/0212; A61B 2018/0268; A61B 2018/0275; A61B 2018/0281; A61B 2018/0287
USPC .......... 606/20–31; 607/96, 98, 99, 104, 105, 607/113, 115, 116
See application file for complete search history.

(56) References Cited

U.S. PATENT DOCUMENTS 6,042,590 A * 3/2000 Sporri .................... A61F 6/225 606/135
7,846,154 B2 12/2010 Bliweis
7,998,139 B2 * 8/2011 Rossetto ............ A61B 18/1815 607/156
2008/0114347 A1 5/2008 Devens et al.
2013/0204241 A1 8/2013 Baust
2017/0135742 A1 * 5/2017 Lee ...................... A61B 18/082
2024/0315750 A1 * 9/2024 Zhang .................... A61B 18/02

FOREIGN PATENT DOCUMENTS

CN 113842202 A 12/2021
WO 2021259379 A1 12/2021
WO 2024196559 A1 9/2024

OTHER PUBLICATIONS

International Search Report and Written Opinion issued for PCT International Application No. PCT/US2024/017854 dated Jul. 8, 2024, 16 pages.

* cited by examiner

*Primary Examiner* — Thomas A Giuliani
(74) *Attorney, Agent, or Firm* — Morgan, Lewis & Bockius LLP; Manita Rawat

(57) ABSTRACT

An ablation probe includes a shell configured to be positioned at a target tissue in a patient and a conduit positioned inside the shell. The conduit is configured to supply a cryo-fluid toward a tip of the probe. The probe also includes a heater positioned radially outward of an outer surface of the shell that is configured to heat the probe to perform thermal ablation.

19 Claims, 7 Drawing Sheets

COMBINATION PROBE FOR CRYOABLATION AND THERMAL ABLATION WITH EXTERNAL HEATER

FIELD

The present disclosure relates to apparatuses and methods for performing cryoablation and thermal ablation with a probe that includes an external heater. More particularly, the present disclosure relates to a probe with an external heater for performing procedures that may include both cryoablation and thermal ablation.

BACKGROUND

This section provides background information related to the present disclosure which is not necessarily prior art.

Systems and methods for providing ablation treatments may include probes that are introduced at or near target tissue in a patient. In traditional systems, a probe may be used in a cryoablation procedure. The probe may be coupled to a cryoablation system. The cryoablation system may include an extremely cold cryo-fluid (liquid, gas, or mixed phase) that may be passed to the probe in thermal contact with the target tissue. Heat from the tissue passes from the tissue, through the probe, and into the fluid that removes heat from the targeted tissue. This removal of heat causes tissue to freeze, resulting in the destruction of the targeted tissue. The cryo-fluid may also be heated subsequent to the freezing cycle. The heating may thaw the frozen tissue to allow the cryoprobe to be removed from the tissue.

Traditional probes may also be used for thermal ablation. The probe used for thermal ablation may include, for example, an RF antenna or a microwave antenna that can be supplied with a suitable power signal to cause tissue at or near the probe to be heated to sufficient temperatures to destroy the target tissue. Traditional or existing probes do not include elements to permit both cryoablation and thermal ablation to be performed by a common probe. In some existing methods, two or more probes must be inserted at the site of the target tissue if different ablation methods are to be performed. There exists a need, therefore, for improved systems, probes, and methods that can allow cryoablation the thermal ablation to be performed by a common probe.

SUMMARY

This section provides a general summary of the disclosure, and is not a comprehensive disclosure of its full scope or all of its features.

In some embodiments of the present disclosure, a combination ablation is provided. The combination ablation probe can be operated to perform cryo cycle and thermal cycles. Both the cryo cycle and the thermal cycle can be ablation cycles that cause the destruction of a target tissue in a patient. The combination probes of the present disclosure may include a heater located external to the probe that can achieve thermal ablation temperatures. The external heater may be configured as a resistive heater embedded or positioned in a layer of material on an external surface of the probe.

In some embodiments, an ablation probe is provided. The ablation probe may include a shell configured to be positioned at a target tissue in a patient and a conduit positioned inside the shell that is configured to supply a cryo-fluid toward a tip of the probe to perform cryo ablation. The ablation probe may also include a heater positioned radially outward of an outer surface of the shell that is configured to heat the probe to perform thermal ablation.

In one aspect, the heater may be embedded in a layer of coating positioned on an external surface of the shell.

In another aspect, the layer of coating may include a thermally conductive material.

In another aspect, the layer of coating may include a thermally conductive heat shrink material.

In another aspect, the heater may include a resistive heating wire coiled around the shell.

In another aspect, the heater may be coupled to a power line configured to supply a power signal to the heater. The power line may be positioned externally to the shell.

In another aspect, the layer of coating may be positioned over the heater and over the power line externally to the shell.

In another aspect, the probe may also include two or more measurement contacts on an external surface of the probe.

In another aspect, the two or more measurement contacts may be positioned in the layer of coating.

In another aspect, the two or more measurement contacts may be configured to collect measurement data regarding operating conditions of the probe.

In another aspect, the heater includes a coil of resistive heating wire and each of the two or more measurement contacts are positioned between adjacent coils of the coil of resistive heating wire.

In another aspect, the two or more measurement contacts may be configured as an array of measurement contacts positioned around a circumference of the external surface of the probe.

In another aspect, the conduit may include at least one opening at or near the tip to allow cryo-fluid to exit the interior of the conduit and flow in a return direction between an outer surface of the conduit and an inner surface of the shell.

In another aspect, the heater may include a coil of resistive wire positioned around a main shaft portion of the shell radially outward of the conduit.

In another aspect, the heater may include a coil of resistive wire positioned around a main shaft portion and the tip of the shell.

In some embodiments, an ablation probe is provided. The ablation probe may include an inner conduit extending axially along an axis and an outer shell positioned radially outward of the inner conduit, extending along the axis and terminating at a tip. The probe may also include a coil of resistive wire positioned externally to the shell. The coil is configured to heat the probe to a predetermined temperature sufficient to perform thermal ablation. The probe further includes a layer of coating positioned around the coil of resistive wire that separates the coil of resistive wire from an external surface of the probe.

In some embodiments, a method of performing an ablation treatment is provided. The method may include positioning an ablation probe at or near a target tissue in a patient and cooling the ablation probe using a cryo-fluid circulated through the ablation probe to cause an ice ball to be formed at the target tissue. The method may also include heating the ablation probe using a heater positioned in a layer of heat conductive material on an external surface of the probe to cause tissue at or near the target tissue to be destroyed.

In one aspect, the step of heating the ablation probe may include heating the ablation probe to a temperature greater than or equal to 150° C.

In another aspect, the ablation probe is not moved after the ablation probe is positioned at or near the target tissue.

In another aspect, the method may also include obtaining measurement data from two or more measurement contacts positioned in the layer of heat conductive material.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
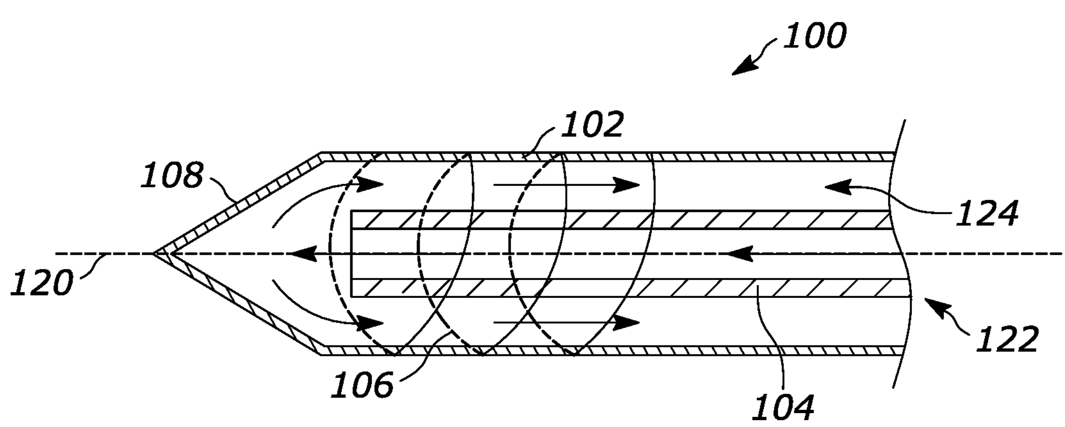
FIG. 1 is a cross-sectional side view of an example ablation probe in accordance with some embodiments of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In various embodiments of the present disclosure, improved ablation probes are provided that incorporate elements that allow the same probe to be used for both cryoablation and thermal ablation. Existing probes are typically limited to use for either cryoablation or thermal ablation but not both. In addition, the extended time for heating cycles of existing probes can dessicate tissues which can result in reduced treatment effectiveness. Still further, existing probes and methods also typically require subsequent procedures that follow ablation procedures because the tissues at the ablation site cannot be returned to sufficient temperatures to perform the follow-up procedure at the same time as the ablation treatment. For example, if a target tissue is located at or near a bone or other support structure of a patient, the structural integrity of the bone or support structure can be compromised when the bone or support structure is subjected to the low temperatures of a cryoablation cycle. Without subsequent treatment, the bone or support structure may fail. A cement or other repair substance may be applied to the bone or support structure to address this condition. Such application of cement or repair substance is applied in a follow-up or subsequent treatment because the tissues typically must be returned to normal body temperatures before the cement or repair substance can be applied. The combination probes of the present disclosure can bring tissues back to normal body temperatures more quickly than existing probes and methods so that the follow-up or repair procedure can be performed in the same session as the ablation treatment.

The combination probes of the present disclosure are improvements over existing probes because the probe can be used for cryoablation and/or thermal ablation without the need to insert a second probe at the target tissue in the patient. Furthermore, the elevated levels of temperature that can be achieved for thermal ablation can also be used for other purposes such as coagulation, cauterization, thawing or other purposes. The combination probes of the present disclosure can achieve higher temperatures than existing cryoablation probes such that the secondary or other purposes such as coagulation, cauterization, thawing and the like can be performed more quickly. This, in turn, can reduce the overall time required for the ablation procedure to reduce risk and improve patient recovery.

In addition, the structure of the combination probes of the present disclosure provides not only thermal capability but also for the inclusion of multiple measurement contacts on the surface of the probe. The measurement contacts may allow measurement data to be collected during treatment that can be used in to make adjustments during treatment to optimize the treatment, improve likelihood of successful treatment outcomes, and to improve patient recovery.

The temperatures required to perform various procedures and/or to achieve desired results may vary according to the types of tissues and/or for bodily structures that may be present at or near a target tissue. In the context of tumors or other undesirable tissues that may be present in a patient, such as for cancer tissue therapy or the like, the cryo and thermal ablation temperature range can span a range from −75° C. to +150° C. The combination probes of the present disclosure can be operated in such a temperature range to achieve desirable temperatures for both cryoablation and thermal ablation. In some examples, the combination probes of the present disclosure can be operated at or below −75° C. during cryoablation cycles to grow ice at a target tissue. The same combination probes of the present disclosure may also be operated at a temperature at or above +150° C. to perform thermal ablation. In still other examples, some ablation probes of the present disclosure can be operated at a temperature at or above +200° C. to perform thermal ablation. In still other examples, other operating temperatures ranges can be achieved.

The combination probes of the present disclosure may also be operated at intermediate temperatures between the cryoablation and the thermal ablation temperatures described above. For example, some example combination ablation probes of the present disclosure can be operated at or near a temperature between about 0° C. and about 20° C. to perform thaw cycles to assist in the removal of the combination probe from an ice ball formed during a cryoablation procedure. In other examples, some combination probes of the present disclosure may be operated at or near a temperature of about 80° C. to about 150° C. to perform a coagulation or cauterization cycle. Such cycles may be used to mitigate, reduce, and/or prevent bleeding that may otherwise occur during or after an ablation procedure.

Referring now to FIG. 1, an example ablation probe 100 is shown. The probe 100 may be used to perform an ablation procedure. The probe 100 may be used to perform ablation procedures that may include both a cryoablation cycle and a thermal ablation cycle. The ablation probe 100 may be positioned at or near a target tissue of patient. The target tissue may be an abnormal or undesirable tissue such as a tumor or other growth.

In the example shown, the probe 100 may include an outer shell 102. The shell 102 may be formed from a thin walled tube that extends from a proximal end at or near a handle (not shown) that can be used by an operator to position the probe 100 at the desired position. The probe 100 may extend from the proximal end to a distal end 108 at a tip of the probe 100. The tip of the probe may be pointed to assist in piercing tissue when the probe 100 is positioned at or near the target tissue in the patient.

The shell 102 may form an inner cavity in which the other elements of the probe 100 can be positioned. In this example, the shell 102 has a circular or rounded cross-section that is axially aligned along axis 120. The shell 102 may be formed of any suitable material such as stainless steel or other suitable material with good thermal conductivity characteristics and bio-compatibility characteristics. A conduit 104 may be positioned inside the shell 102. The conduit 104 may be a tubular structure that is axially aligned along the axis 120. The conduit 104 can be used to form a pathway for a cryo-fluid to flow into and out of the probe 100. The conduit 104 may include an inner channel 122 that is located inside the conduit 104 that is defined by the inner surface of the conduit 104. The conduit 104 may also define a return channel 124 that is defined by the outer surface of the conduit 104 and the inner surface of the shell 102. The cryo-fluid may flow into the probe 100 through the inner channel 122 and out of the probe 100 through the return channel 124 as shown by the arrows on FIG. 1.

The cryo-fluid can be supplied by a suitable cryo-fluid source that can supply the cryo-fluid to the probe 100 during a cryoablation cycle. During such a cryoablation cycle the cryo-fluid can flow into the probe 100 and out of the inner channel 122 at or near the distal end 108 of the probe. In some examples, the probe 100 can be configured as a Joule-Thompson cryoablation probe in which the cryo-fluid expands at the distal end 108 causing a rapid drop in temperature of the cryo-fluid. The cryo-fluid can cause the temperature of the shell 102 to rapidly drop removing thermal energy from the tissue surrounding the probe 100. An ice ball may form at the distal end 108 of the probe 100 to destroy target tissue at the distal end 108 of the probe 100. In other examples, the probe 100 may be configured as other types of cryoablation probes such as supercritical, near critical, or other type of cryoablation probe to cause ice to form at the target tissue.

During the cryoablation cycle, the cryo-fluid may flow away from the distal end 108 of the probe 100 through the return channel 124. The return channel 124 may have an annular shape positioned radially outward of the conduit 104. The cryo-fluid may be any suitable fluid, gas, or combination of fluid and gas that can be operated at temperatures sufficient to cause ice to form at the probe in a sufficient time frame to support cryoablation procedures. In various examples, the cryo-fluid may be argon, nitrogen, helium, or the like.

As further shown in FIG. 1, the probe 100 may also include heater 106. The heater 106, in the example shown, is a resistive heating coil that is coiled or wrapped around around the axis 120. The heater may be a coil of resistive wire that is embedded in a layer or coating external to the shell 102. The coil may include a plurality of wraps of resistive wire. The wraps may be concentrically positioned around an axis of the probe 100. In other examples, the heater may be positioned in other positions but is located radially outward of the conduit 104 and/or the shell 102. As can be seen, the heater 106 is not located in the cryo-fluid path such that it is not in direct thermal communication with the cryo-fluid in the supply pathway 122 or the return pathway 124 inside the probe 100.

The heater 106 can be made of a suitable resistive wire that can heat when a current is supplied. The heater 106 can be coupled to a suitable power supply located outside of the probe 100. Suitable wire leads can be positioned, embedded, or otherwise formed in the probe 100 to couple the heater 106 to the power supply (not shown). During a heating or thermal ablation cycle, a power signal can be supplied to the heater 106 to raise the temperature of the heater 106. The heater 106 may be covered or embedded in a thermally conductive layer while separating the resistive wire from the shell and the outer surface of the probe. The supply of power to the heater 106 can cause the temperature of the wire to increase and can allow the thermal energy to be transferred via the coating or layer of material to the tissue external to the probe during treatment. The temperature can be raised to a temperature sufficient to thermally ablate the target tissue. In some examples, this temperature is at or greater than 150° C. In other examples, the probe 100 can reach temperatures of 200° C. or greater. In yet other examples, the probe 100 can reach temperatures of 240° C. or greater.

Existing or traditional probes may include a heater to assist with the heating of cryo-fluid. The heating of the cryo-fluid in such traditional probes may assist in a thaw cycle to improve the speed at which the probe may be withdrawn from the ice ball that is formed during the cryoablation cycle. Such traditional probes cannot reach thermal ablation temperatures such as example probe 100 and the other combination ablation probes described in the present disclosure. The probe 100 and others described herein may thermally conduct heat from the heater 106 to the target tissue to cause thermal ablation at the location of the probe 100. In addition, the probe 100 can be operated to heat the localized area of the probe 100 for thermal ablation without the existence or flow of a fluid inside in the probe 100. Still further, a thaw cycle or other heated cycles can be more rapidly performed using the probes of the present disclosure because of the increased heating capacity and heating functionality of the combination probes of the present disclosure.

Figure 2:
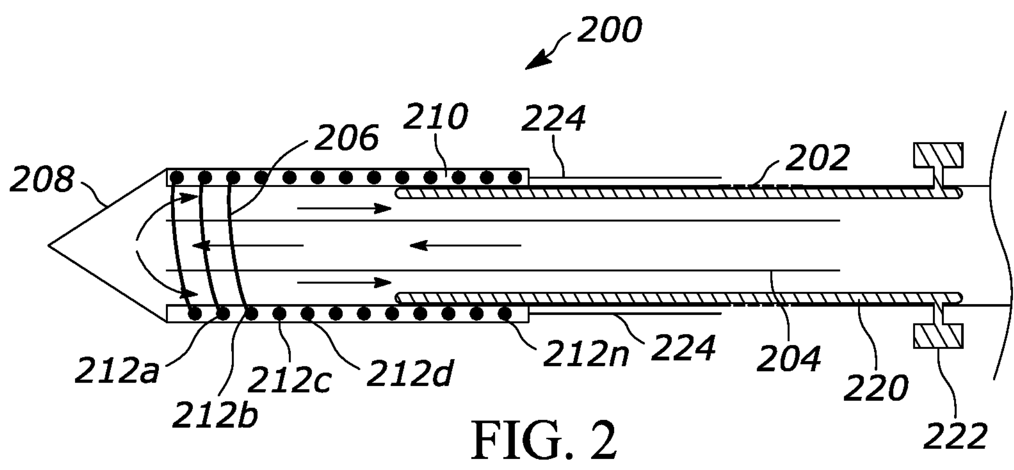
FIG. 2 is a cross-sectional side view of another example ablation probe in accordance with some embodiments of the present disclosure.

Referring now to FIG. 2, another example probe 200 is shown. The example probe 200 may include a shell 202, a conduit 204, and a heater 206. The probe 200 may use these features to operate as described above with respect to probe 100. The probe 200 may be configured as previously described to allow the probe 200 to operate and perform both cryo-ablation cycles and thermal ablation cycles.

The heater 206 of probe 200 may be constructed of a coil of resistive wire. The coil may include one or more wraps 212*a*, 212*b* to 212*n*. The coil may include any suitable number of wraps 212 so as to extend along a predetermined distance of the shell 202 as may be desired to heat a predetermined length of the probe 200. In some examples, the coil may be a single integrated coil of resistive wire that can be heated by energizing the coil with a suitable power signal from a power supply. In other examples, the coil can be separated into multiple separate coils that can be energized independently from one another to provide localized heating a position on the shell 202 as may be desired.

The wraps 212 can be positioned radially outward of the external surface of the shell 202. In such an arrangement the diameter of the wraps 212 can be greater than the outer diameter of the shell 202. In some examples, the shell 202 can have a recessed portion, depression, cavity, groove, or other outer shape in which the coil of wraps 212 can be positioned. This may allow the outer surface of the probe 200 to have a smooth or uninterrupted outer profile. Such a smooth outer profile can assist in allowing the probe 200 to be inserted through tissue without undue interference.

The heater 206 may be coupled to a suitable power supply using power lines 224. The power lines 224 can be used to convey a power signal from the power supply to the heater 206. In this example, the power lines 224 are positioned externally to the shell 202. The probe 200 may include various quantities of power lines as may be needed to power individual heaters 206 if more than one heater 206 is provided or if the heater 206 is divided into multiple independently controllable heating zones.

The probe 200 may also include a layer of material 210 that is positioned over and/or around the coil of wraps 212. While not shown, the layer of material may also be deposited or positioned over and/or around the power lines 224. The layer of material can be made of a thermally conductive material that can allow for an efficient transfer of thermal energy from the heater 206 to the external surface of the probe 200. The layer of material 210 can be coating that is applied to an external surface of the probe or a layer of heat shrink material that can be positioned over the heater 206 and then heated and fixed into position.

The layer of material 210 can provide a smooth outer surface to assist in the positioning of the probe 200 at the target tissue. The layer of material 210 may also operate to efficiently conduct thermal energy from the heater 206 and distribute the thermal energy along a longitudinal area of the probe 200. Still further, when the probe 200 is operated to perform a cryo cycle. The layer of material can operate to conduct heat away from the target tissue and into the cryo-fluid that is being moved through the internal passages of the probe 200. The layer of material can efficiently conduct thermal energy from an exterior of the probe 200 to the internal passage of the probe 200 through the shell 202.

As further shown, the probe 200 may include an insulating sleeve 220. The insulating sleeve 220 can be positioned inside the shell 202 and may be made of a heat or thermal resistant material. In some examples, the insulating sleeve can be a vacuum sleeve. The insulating sleeve 210 can be positioned between the internal chamber or passage of the probe 200 and the shell 202. The insulating sleeve 210 can operate to reduce the amount of thermal energy that is transferred through the shell 202 to the cryo-fluid that may be positioned and/or flowing through the probe 200. The insulating sleeve 210 can be used to control or determine a size of the ice ball that is created when the probe 200 is performing a cryo cycle. Insulating sleeve 210, in some examples, can be adjustable or moved axially along the longitudinal length of the shell 202. The adjustment of the insulating sleeve 210 can be used to adjust, control, the size of the ice ball that is created during a cryo cycle. The insulating sleeve 210 can be coupled to an adjustment mechanism 222. The adjustment mechanism 222 can be used to move the insulating sleeve 210 axially in the shell 202. The adjustment mechanism can include a button and one or more detents that can be used by an operator to move the insulating axially and lock the insulating sleeve in a desired position to achieve an ice ball of predetermined size. In other examples, the adjustment mechanism may include a knob that can adjustably move the insulating sleeve 210 axially in the sleeve 210. In still other examples, other suitable adjustment mechanisms can be used.

Figure 3:
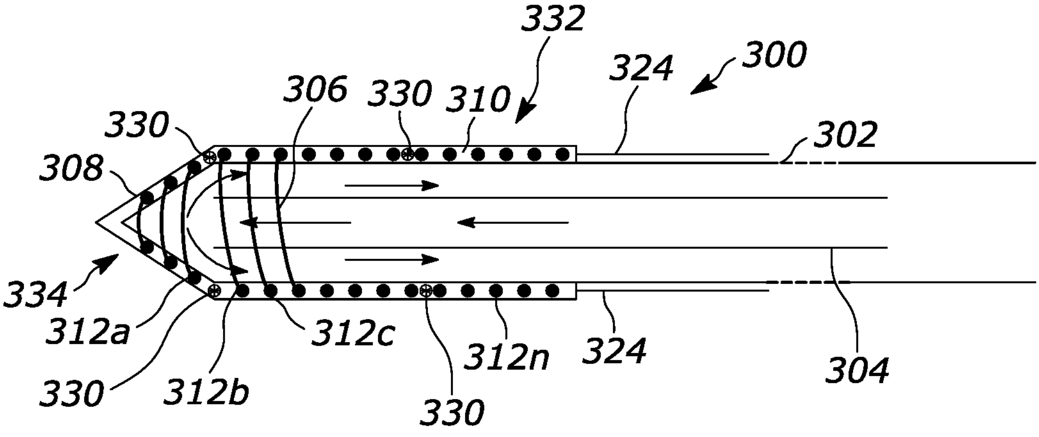
FIG. 3 is a cross-sectional side view of another example ablation probe in accordance with some embodiments of the present disclosure.

Turning now to FIG. 3, another example ablation probe 300 is shown. The probe 300 is similar in many respects to the probe 200 previously described. The probe 300 includes a shell 302, a conduit 304, and an external heater 306. The probe 300 can be operated to perform both cryo cycles for cyro ablation and thermal cycles for thermal ablation. Conduit 304 is positioned inside the shell 302 to allow cryo-fluid to be supplied into the probe 300 toward the distal end where the cryo-fluid may exit the conduit 304 and flow away from the distal end 308 through a return passage located between the conduit and the shell 302. During the flow of cryo-fluid, an ice ball may form at or near the distal end 308 to perform a cryo ablation procedure.

The probe 300 may also be operated in a thermal cycle to perform thermal ablation and/or to perform a thaw, coagulation, cautery or other thermal operation. The heater 306 may include a coil of resistive wire that is positioned externally to the shell 302. The heater 306 may be positioned around an external surface of the shell 302, for example. The layer of material 310 may be positioned over and/or around the one or more wraps 312 of the heater 306. The layer of material can be configured as previously described with respect to probe 200.

In this example, the heater 306 is positioned along a main body portion 332 of the shell 302 as well as on the tip portion 334. The main body portion 332 can be a portion of the shell 302 that is elongated and has substantially the same diameter along its length. The tip portion 334 of the shell 302 is positioned at a distal end 308 of the shell 302 can be tapered to a point and may have a varying diameter along its length. The wraps 312 of the heater 306 are wound around both the tip portion 334 and the main body portion 332 in this example. The heater 306 may be positioned and/or wound as may be desired to allow the probe 300 to have a heating zone as may be desired to reach or be positioned at or near a target tissue. The heater 306 may be coupled to a power supply using one or more power lines 324. The power lines 324 can be positioned externally to the shell 302.

The probe 300, in this example, also includes two or more measurement contacts 330. The measurement contacts 330 can be sensors, electrical contact points, or the like that can be used to collect measurement data at or near the probe 300. The measurement data can collect information about the operating conditions of the probe 300. The measurement contacts 330 can be positioned on an external surface of the probe 300. The measurement contacts 330 can be coupled to a control, computing device, and/or suitable data acquisition unit via measurement leads (not shown) that can extend externally along the shell 302. The measurement leads can be covered and/or positioned under the layer of material 310.

In various examples, the measurement contacts 330 can measure temperature, impedance, pressure, mechanical bending force, strain, or the like. The measurement contacts 330 can be positioned between the wraps 312 of the heater 306 in some examples. The measurement contacts 330 can be positioned in a manner as may be desired to collect information from various positions at or around the probe 300.

Figure 4:
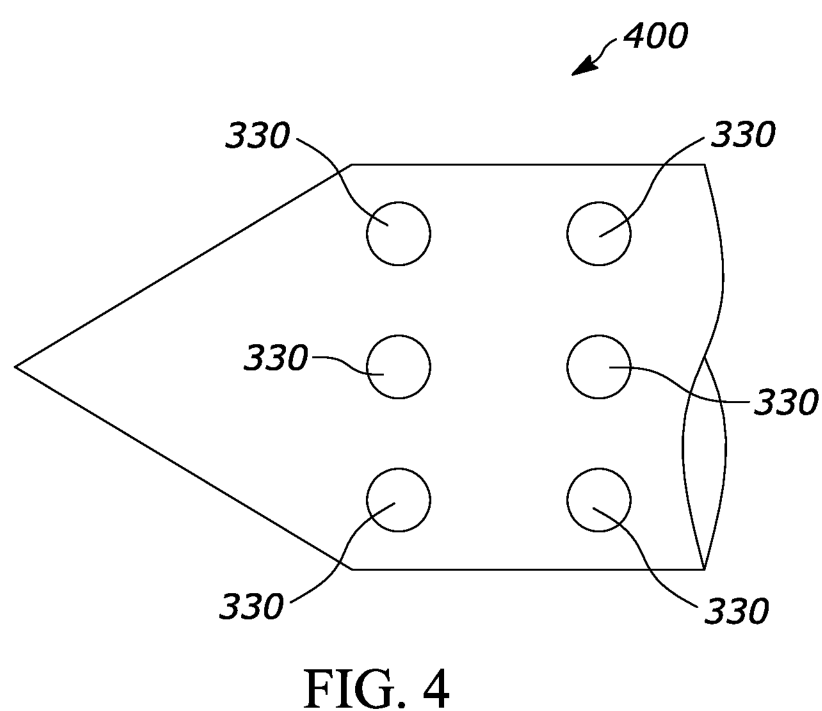
FIG. 4 is an illustration of an example probe of the present disclosure that includes an array of measurement contacts on the external surface of the probe.
Figure 5:
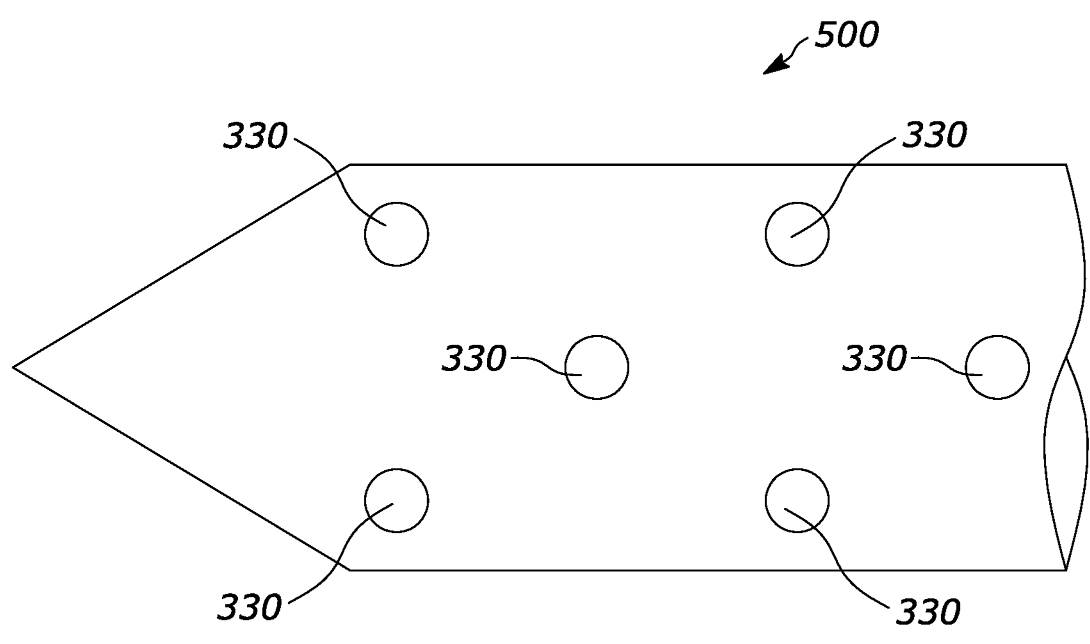
FIG. 5 is an illustration of another example probe of the present disclosure that includes an offset array of measurement contacts on the external surface of the probe.

The measurement contacts can be positioned in the layer of material 310 and can be exposed to the external surface of the probe 300 to collect measurement data. The measurement contacts 330 may be arranged in a suitable array to collect the measurement data. In one example, the measurement contacts 330 may be arranged in an aligned array 400 in which the measurement points 330 are arranged in rows and are spaced apart along an axial length of the probe 300 as well as circumferentially around the probe 300 as illustrated in FIG. 4. In another example, the measurement points 330 may be arranged in an offset array 500 in which the measurement points are offset relative to neighboring rows as illustrated in FIG. 5. In other examples, other arrays can be used to distribute the measurement points along the axial length of the probe 300 and around the circumference of the probe 300.

The ablation probes of the present disclosure, such as probes 100, 200, and 300 are improvements over existing probes. The probes of the present disclosure can be operated in both a cryo ablation mode of operation and in a thermal ablation mode of operation. Additionally, the structure of the probes of the present disclosure allow for simplified and lower cost assembly and/or manufacturing. Many existing probes include internal features that need to be sized and assembled within the inside of the shell. In the present disclosure, the probes include a heater that is positioned externally to the shell. This allows for simplified manufacturing. In addition, the probes of the present disclosure can be reduced in size over existing or traditional probes to have reduced outer diameters. This can allow reduced impact to the patient during treatments and can improve results and patient recovery.

Figure 6:
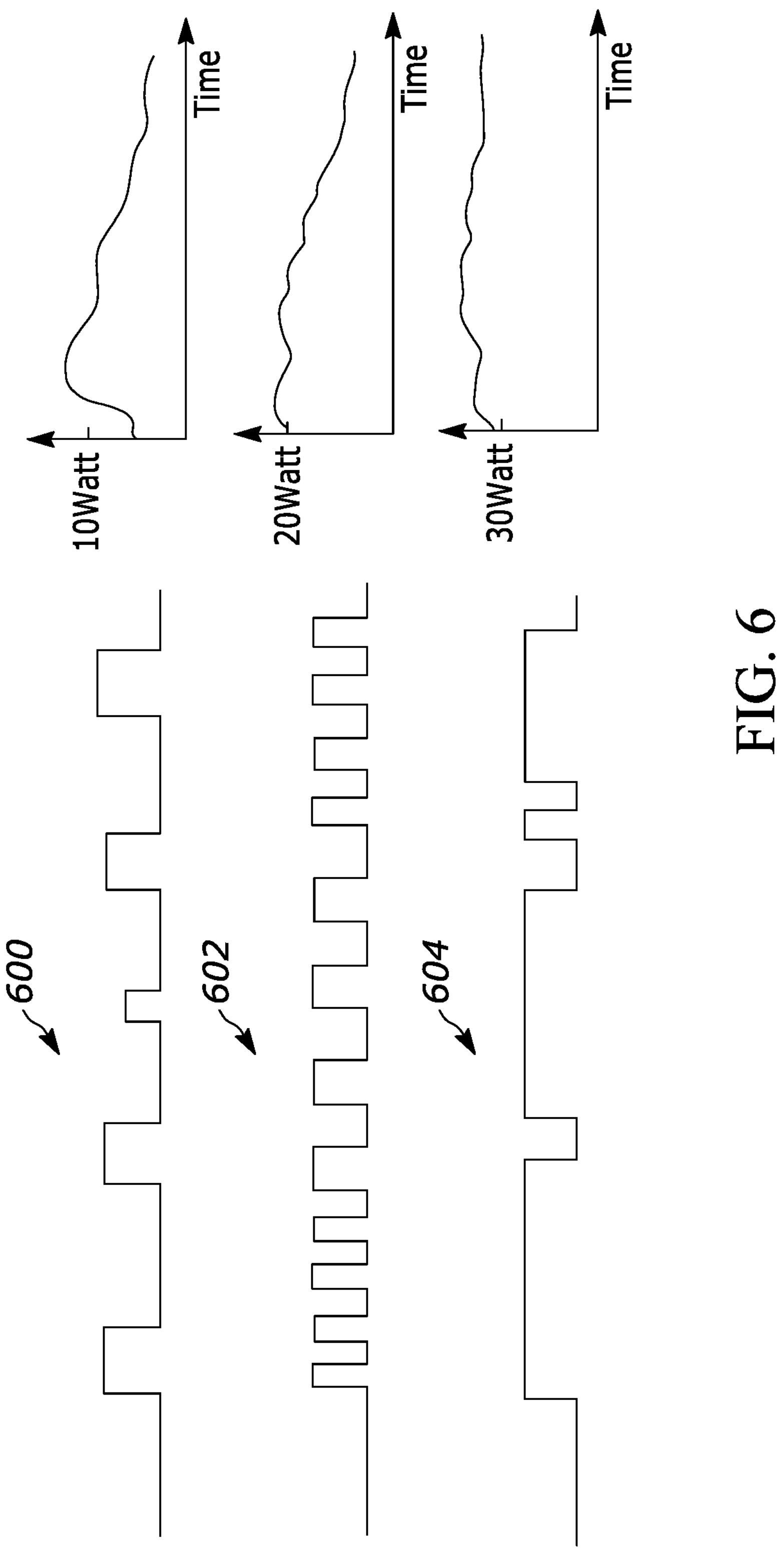
FIG. 6 is an illustration of example power signals that can be used to energize the heaters of the ablation probes of the present disclosure.

Referring now to FIG. 6, example power signals 600, 602, and 604 are shown. The heater of the probes of the present disclosure can be powered to heat the probe to temperatures in excess of 200° C. The power signal used to perform thermal ablation, coagulation, cauterization, and thaw operations can use different cycles. As will be further described, the power supply that is coupled to the heater of the probes can be adjustable and controllable to achieve and/or maintain desired treatment temperatures and durations.

For example, the power signal 600 may be used to perform a thaw cycle to quickly permit the needle of the probe to be moved or withdrawn from an ice ball that was formed during a cryo cycle. Such a thaw cycle may use a 10 W signal with pulsed modulation as shown. The power signal 602 may used to achieve a faster thaw cycle and/or to perform a coagulation cycle. Since higher temperatures are needed, the power signal 604 may include a 20 W signal with a more frequent pulse than that used for the thaw cycle shown for power signal 600. The power signal 604 may be used for thermal ablation or for cauterization. This type of operation requires even higher temperatures than the thaw or coagulation cycles. In this instance, a 30 W signal may be used and the pulse widths may be larger to generate enough thermal energy to achieve the elevated temperatures (e.g., 150° C. to 200° C.) for thermal ablation and/or cauterization. In other circumstances, the power supply that is coupled to the probes of the present disclosure may deliver other suitable power signals with different pulse widths, amplitudes, frequencies, or other characteristics as may be desired to achieve the desired operating conditions.

Figure 7:
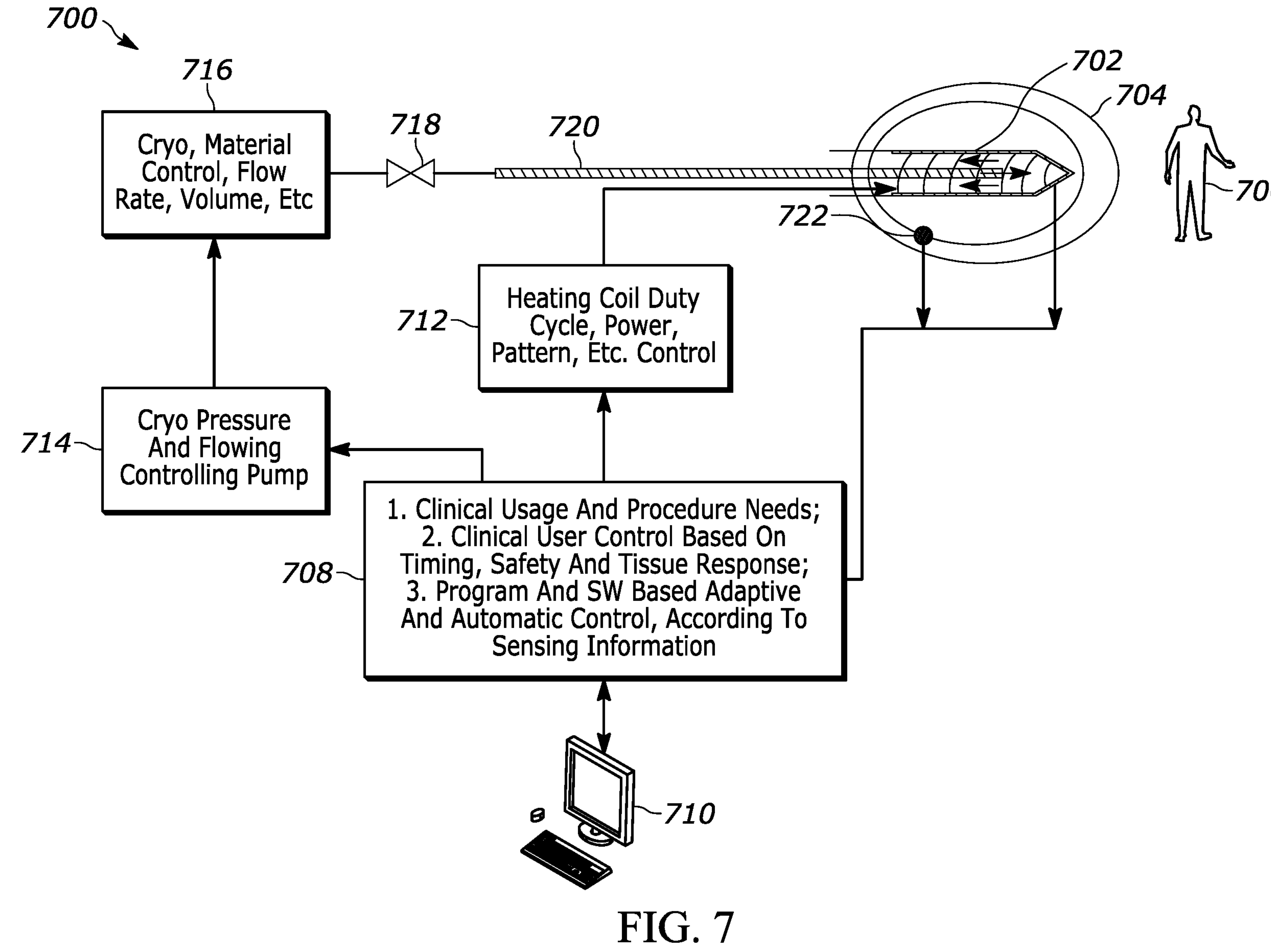
FIG. 7 is a diagram illustrating an example ablation system that can be used with the example ablation probes of the present disclosure.

Turning now to FIG. 7, and example combination ablation system 700 is shown. The cryoablation system 700 may include a cryoablation computing device 710, a combination control 708, a cryo-fluid pump 714, a cryo-fluid source 716, an inlet valve 718, a cryo-fluid supply 720, a combination probe 702, and a controllable power supply 712. The cryo-fluid pump 714, the cryo-fluid source 716, the inlet valve 718, the cryo-fluid supply 720, the combination probe 702 may operate to deliver a cryo-fluid from the cryo-fluid source 716 to the probe 702 to perform a cryoablation cycle in one mode of operation. The cryo-fluid (e.g., argon, helium, or nitrogen) can be stored in the cryo-fluid source 716, such as a dewar or other suitable container, and then delivered to the probe 702 via the cryo-fluid supply 720. The cryo-fluid may expand at a tip of the probe 702 and cool the tip of the probe 702 to a temperature at which the tissue of a patient 706 begins to freeze forming an ice ball 704. The probe 702 can be positioned at or near a target tissue (e.g., a tumor) in the patient. In this manner, the target tissue can be frozen destroying the target tissue.

The combination ablation system 700 can also be operated in a second mode of operation to perform a thermal ablation treatment. The second mode of operation can also be used to perform a thaw cycle, a coagulation cycle, a cauterization cycle, or other cycle in which the probe 702 is heated. The power supply 712 can be used to energize the heater located external to the shell of the probe 702. The probe 702 can include a structure as previously described to allow the external heater to heat the external surface of the probe 702. The probe 702 may be used to reach temperatures greater than 150° C. in some examples, and greater than 200° C. or 240° C. in other examples.

The combination ablation system 700 is an improvement over existing or traditional systems in that the system can be operated in either mode of operation to perform cryo cycles and thermal cycles repeatedly using a single probe. The system 700 can perform cryoablation treatments, thermal ablation treatments, or both during a single procedure. Such flexibility and functionality can allow ablation treatment to be performed during a single procedure to improve treatment effectiveness. Furthermore, the thermal cycles can also be performed more quickly than coagulation cycles or thaw cycles using traditional system of probes because the probe 702 can be heated more quickly.

A treatment plan can be determined prior to the performance of an ablation treatment. The treatment plan can detail and/or describe the various steps of the process and various aspects of the treatment such as the types of equipment to be used, a positioning of the probe, temperatures of the probe, duration of cryo and thermal cycles as well as a quantity of cycles. The treatment plan may be determined by a medical professional and/or by others. In some examples, the ablation computing device 710 may determine or recommend a treatment plan after health, patient, and other information is input into the ablation computing device 710 or is retrieved or otherwise obtained by the ablation computing device 710.

As further shown in FIG. 7, the control 708 may be coupled to the probe 702 and/or the measurement contact 722. The control 708 may collect measurement data from the probe 702 and/or the measurement contacts 722 regarding temperatures of the target tissue and/or temperatures of the probe 702 during a treatment. The probe 702, in this example, may include multiple measurement contacts or other sensors. The impedance measurements can be used to determine a temperature, or other condition of the patient, such as a bleeding condition. The measurement contacts 722 may be as previously described or may be any suitable sensor such as an impedance sensor, temperature sensor, or the like. The measurement data from the measurement contacts 722 and/or the probe 702 can be sent to the control 708 and/or the computing device 710 and stored or processed as needed.

The control 708 can be any suitable controller, PLC, data acquisition unit or other control unit. The control 708 is operable not only to receive impedance and/or other measurement signals but may also be operable to control, change or adjust operating parameters of the ablation system 700. For example, the control 708 may be operable to control the power supply 712 to energize the external heater of the probe 702. The control 708 may change, adjust or control the voltage, current, power profile, frequency and timing of the power delivered to the external heater of the probe 702. Such control can be used, for example, to manage thermal cycles of the ablation system 700.

The control 708 is also coupled to the cryo pump 714 and other elements of the ablation system 700 that operate the flow of cryo-fluid to the probe 702 during a cryo cycle. The control 708 can operate to manage and control the flow of cryo-fluid and the operating conditions of the cryo-fluid to create the ice ball 704 to form during a cryo cycle.

The computing device 710 can be any suitable computing device that can operate to receive and process data and provide instructions to the control 708. The computing device 710 may be, for example, a suitable workstation, computer, laptop, tablet, server or the like.

Figure 8A:
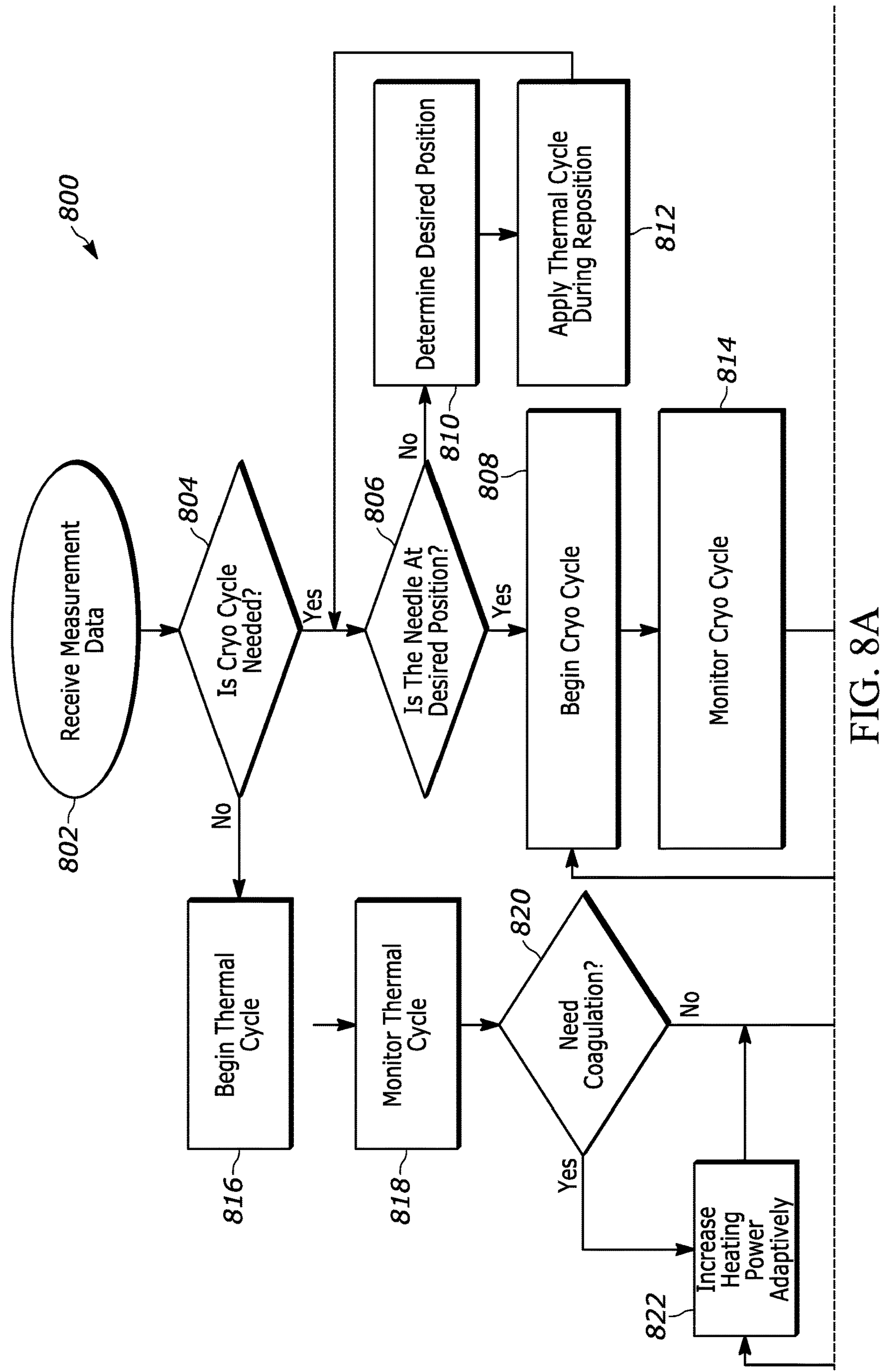
FIGS. 8A and 8B are a flow chart illustrating an example method of performing an ablation procedure.
Figure 8B:
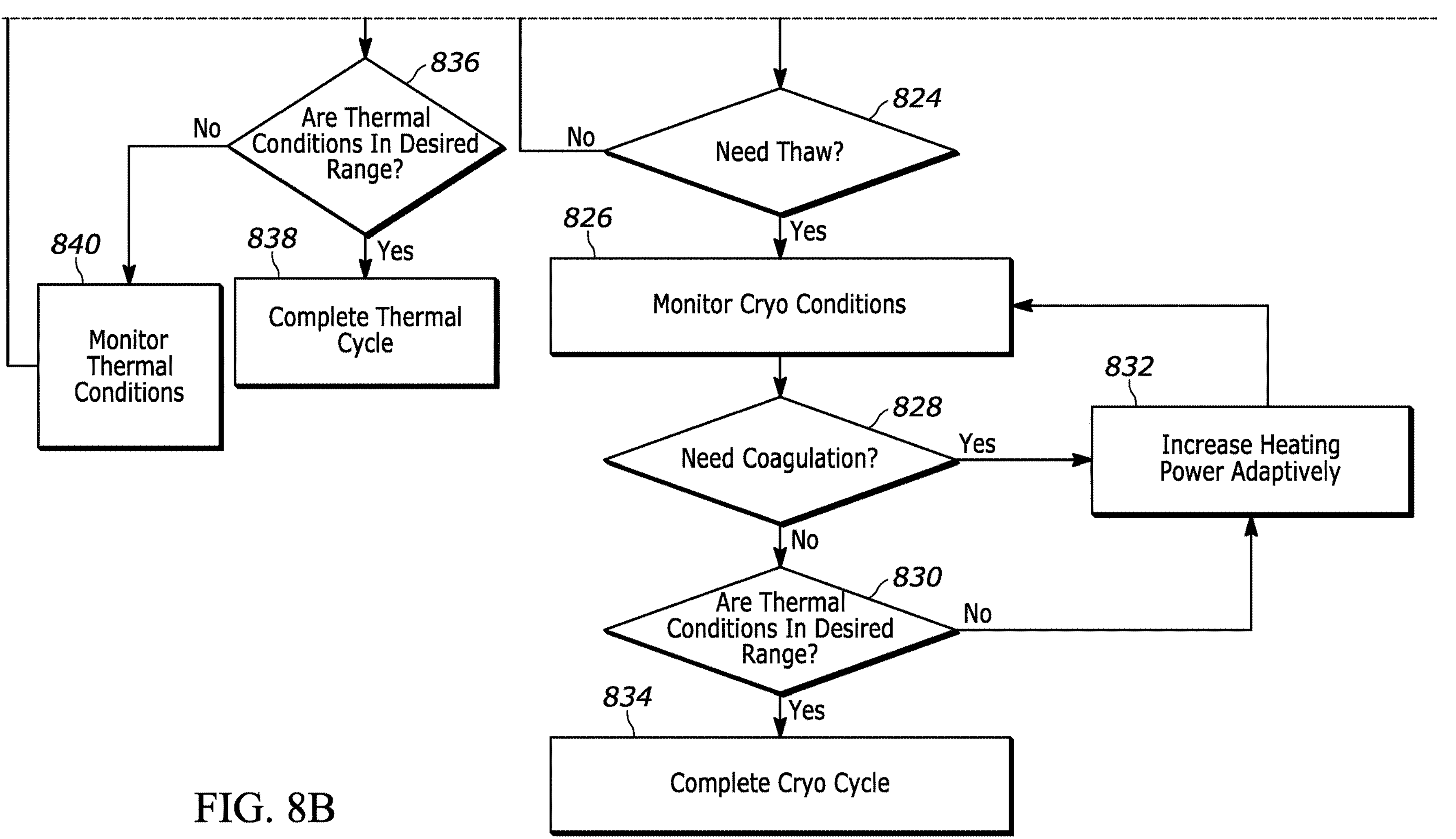

Referring now to FIG. 8, an example method 800 of performing an ablation procedure is shown. The method 800 may be performed using the combination ablation system 700 previously described. Other systems and apparatuses may also be used. The description below describes the method 800 being performed by the system 700 but it should be appreciated that other systems and apparatuses can also be used.

The method 800 may begin at step 802. At step 802, measurement data is received. The measurement data may be received from the measurement contacts of the probe 702 or from elsewhere regarding conditions of the patient and of elements of the ablation system 700. The measurement data may be used to determine whether conditions are in desired operating ranges and/or the patient conditions are in proper ranges to begin an ablation treatment. Such measurement data may be compared with a treatment plan or other information that is obtained by the computing device 710.

At step 804, it is determined whether a cryo cycle is needed. The computing device 710 may have obtained a treatment plan and such plan may indicate whether a cryo cycle is needed. In other circumstances, a medical professional may determine whether a cryo cycle is needed. If a cryo cycle is needed, the method 800 may proceed to step 806. If a cryo cycle is not needed, the method 800 may proceed to step 816.

At step 806, the computing device 710 may determine if the needle of the ablation probe is at a desired position. In other examples, a medical professional may determine if the needle of the ablation probe is at the desired position. Imaging may be performed and such images may be obtained by the computing device 710. The images may be compared to a pre-treatment image and/or to the treatment plan to determine if the probe is positioned at or near the target tissue. There may be other body structures near the target tissue and the probe's position to these other body structures may be determined before an ablation cycle is performed. If the probe is positioned at a desired position, the method 800 moves to step 808. If the probe is not positioned at a desired position, the method 800 moves to step 810.

At step 810, a new desired position of the probe may be determined. In some examples, the computing device 710 may determine the new desired position. In other examples, a medical professional may make such determination. The new desired position may be indicated in the treatment plan.

The computing device 810 may determine, for example, that the probe needs to be retracted, re-positioned, or otherwise moved in order to position the probe in a desired location relative to the target tissue and/or positioned away from a neighboring body structure such as a blood vessel.

At step 812, the computing device 710 and/or the control 708 may cause a thermal cycle to be initiated during re-positioning of the probe. It may be desirable to initiate a thermal cycle so that cauterization can be performed during re-positioning. Such a cautery thermal cycle may be desirable because the probe may have contacted undesirable cells, such as cancer cells. The cautery thermal cycle can reduce a likelihood that the undesirable cells are moved or migrated to another location in the patient. The cautery thermal cycle may also reduce a likelihood of bleeding during the re-positioning.

The cautery thermal cycle may be initiated by the control 708 that can cause a power signal from the power supply 712 to be supplied to the external heater of the probe 702. The power signal may be in the range of about 15 Watts to about 50 Watts (W), for example. The cautery thermal cycle may also have a predetermined duration. In some examples, the cautery thermal cycle may have a duration of about 15 to about 120 seconds. In other examples, other durations may be used. The thermal cycle performed at step 812 may prevent and/or reduce a bleeding condition that may occur when a needle is repositioned. The thermal cycle at step 812 may also prevent a migration of harmful tissue or cells from occurring during the respositioning of the needle.

After respositioning and a thermal cycle, the method 800 may then return to step 806 where the position of the needle is confirmed. If the re-positioned needle is in the desired position, the method may proceed to step 808. If the needle still is not at the desired position, the needle can again be repositioned following the steps 810 and 812 as previously described.

At step 808, the computing device 710 and/or control 708 may begin a cryo cycle. The control 708 may cause cryo-fluid to be supplied to the probe 702 at a predetermined temperature and pressure. Such flow can cause an ice ball to form at the distal end of the probe 702. The method 800 may then proceed to step 814.

At step 814, the ablation system 700 may monitor the cryo cycle. During such monitoring, measurement data may be collected regarding the ablation conditions at the probe 702 and/or of the patient 706. For example, temperature, pressure, flow rate, ice ball size, ice ball growth or the like can be collected and compared against predetermined thresholds or predetermined ranges by the computing device 710. This measurement data may be collected from the measurement contacts in the probe 702. The predetermined ranges, thresholds or other operating parameters may be determined prior to the treatment being performed. Such information may be obtained in a treatment plan, for example. The treatment may also include information regarding a number and duration of cryo and/or thermal cycles that are to be performed. This information can be compared to the information and/or measurement data obtained at step 814. After step 814, the method 800 may proceed to step 824.

At step 824, the computing device 710 and/or the control 708 may determine whether a thaw cycle is needed. The thaw cycle may be prescribed or included in the treatment plan. In other circumstances, the computing device 710 and/or operator may determine that a thaw cycle is needed. A thaw cycle may be needed, for example, if the cryo cycle has ended, the probe is to be withdrawn or the size of the ice ball is growing too fast or too large than may be needed or desired. If the computing device 710 (or user) determines that a thaw cycle is needed, the method may proceed to step 826. If it is determined that a thaw cycle is not needed, the method 800 may proceed back to step 808, wherein the cryo cycle is continued or repeated until such time that a thaw cycle is needed.

At step 826, the heater of the probe may be energized to heat the probe and the conditions of the cryo cycle are continued to be monitored. The power that is supplied at step 826 may be adjusted, changed, or maintained depending on the measurement data that is obtained by the control 708 and/or the computing device 710. The temperature of the probe, impedance, and/or size of the ice ball may be monitored and compared to thresholds or ranges as previously described. The control 708 may take action to cause the probe to heat as desired in order for conditions to be maintained or achieved as desired.

At step 828, the computing device 710 may determine whether a coagulation cycle is needed. The computing device 710 may receive impedance measurement from the probe and/or other sensor in the region of the treatment. The impedance, for example, may provide an indication of whether a bleeding condition is present. The computing device 710 may determine that a coagulation cycle is needed if the measurement data indicates that a bleeding condition is present. If a coagulation cycle is needed, the method may proceed to step 832. If no coagulation cycle is needed, the method 800 may proceed to step 830.

At step 832, the computing device 710 and/or the control 708 may increase heating power to the external heater of the probe. The control 708 may send an instruction to the power supply 712 to increase the power supplied to the heater. The control 708 and/or the computing device 710. The power may be increased, for example, until the temperature of the probe achieves a predetermined temperature threshold or a predetermined temperature range. The method 800 may then return to step 826 to repeat steps 826 and 828.

At step 830, the thermal conditions of the probe and/or the patient may be monitored. The probe may be removed from the target tissue and/or the ice ball at this stage of the cryo cycle after all cycles (e.g., cryo and/or thermal) have been completed. The system may continue to monitor the thermal conditions to determine if a bleeding condition is present. In other circumstances, it may be desirable to perform a cautery cycle if the probe is being removed. Such a cautery cycle can prevent or reduce the likelihood of a bleeding condition when the probe is removed. If such additional heating is desired and/or needed, the method may proceed to step 832. At step 832, the control 708 and/or the computing device 710 may increase power to the external heater of the probe to increase heating to perform a coagulation or cautery cycle as may be desired. If the thermal conditions are in desired ranges and the duration and quantity of cryo and/or thermal cycles is complete, the method 800 may move to step 834 where the cryo cycle is complete. While not shown, the method may move back to the start to perform more cryo cycles as may be desirable for particular ablation treatments.

As previously discussed, at step 804, the computing device 710 may determine that a cryo cycle is not needed. The computing device 710 may determine that a thermal cycle is needed. The treatment plan or medical professional may determine that a thermal cycle is needed in other examples. A thermal cycle may begin at step 816. To begin the thermal cycle, the computing device 710 and/or control 708 may cause the power supply 712 to deliver a power signal to the external heater of the probe. This may cause the probe to begin to heat as heat is transferred from the heater through the layer of material covering the heater.

The method 800 may then move to step 818. At step 818, the computing device 710 and/or control 708 may monitor the thermal cycle. Measurement data that include impedance information, temperature information, power information, patient information, and the like may be received and monitored by the computing device 710 as previously described. The measurement data may be compared to predetermined thresholds and/or predetermined ranges in order to achieve a desired result such as the thermal ablation of a target tissue in the patient. As such, the probe may reach temperatures in excess of 150° C. In other examples, the probe may reach temperatures in excess of 200° C.

At step 820, the computing device 710 may determine whether a coagulation cycle is needed. The coagulation cycle at step 820 may be performed if a bleeding condition is detected. The coagulation cycle at step 820 may be performed similarly to step 828 previously described. If a coagulation cycle is needed the method may proceed to step 822 where power is adjusted to achieve a desired temperature to promote coagulation. If no coagulation is needed, the method 800 may proceed to step 836.

At step 836, the computing device 800 and/or the control 708 may monitor the thermal conditions to determine if the conditions are in the desired range(s). The computing device 800 may determine this by receiving the measurement data and comparing the measurement data to predetermined thresholds or predetermined ranges. If the thermal conditions indicate, the thermal cycle has achieved the predetermined limits, thresholds, and/or ranges, the thermal cycle may proceed to step 838 at which time the thermal cycle may end. The limits, thresholds and/or ranges may include duration, temperature, impedance, and the like. If the computing device determines that thermal conditions have not achieved the cycle requirements, the method 800 may move to step 840 at which time the computing device can continue to monitor the thermal conditions and to adjust the power to the external heater of the probe at step 822 as may be necessary to achieve the cycle requirements.

As with the previously described cryo cycle, the thermal cycle in method 800 may be repeated a suitable number of times as may be desired. Thermal cycles and cryo cycles may be alternated, repeated, or varied to achieve a desired result during an ablation treatment.

Figure 9:
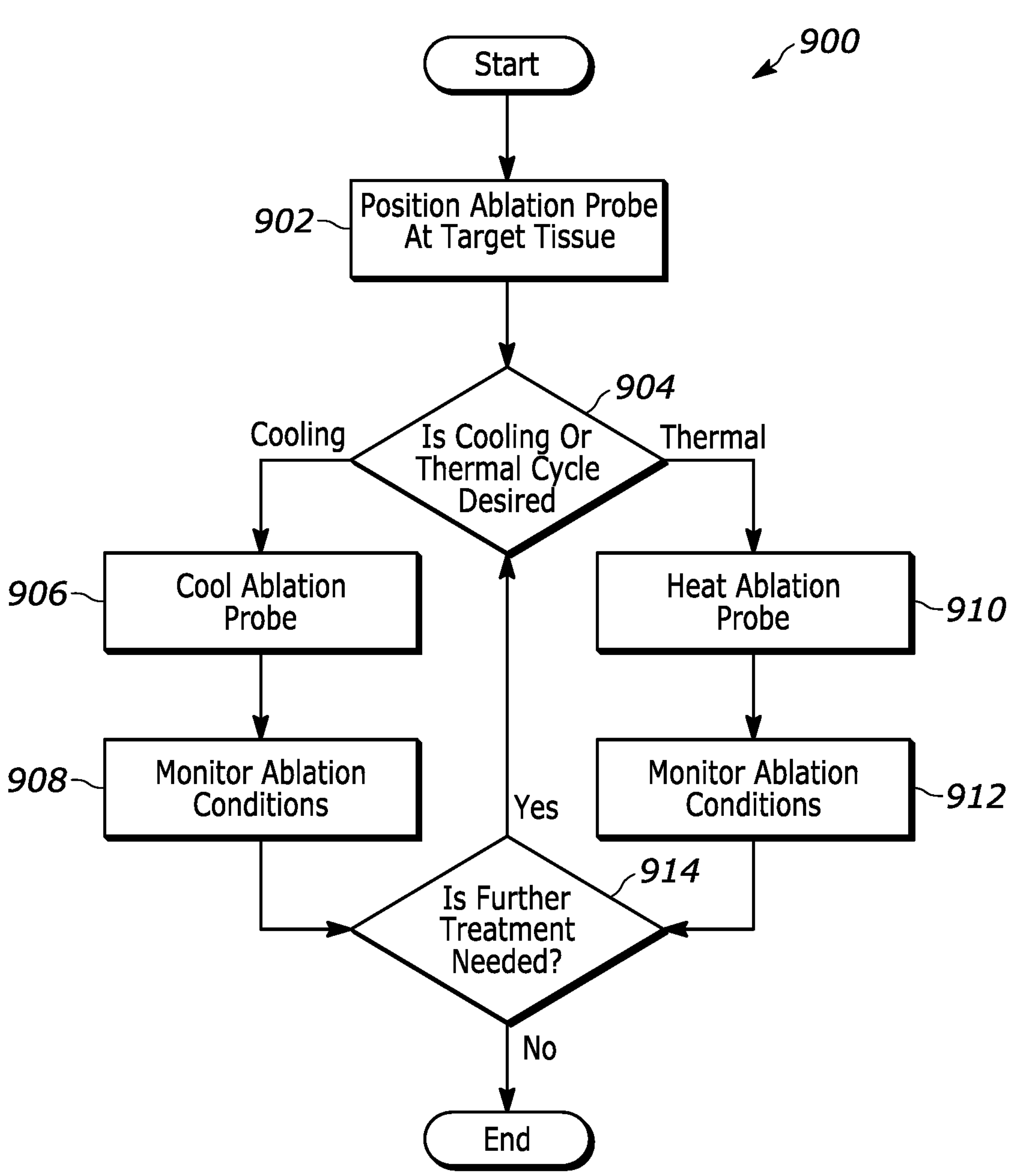
FIG. 9 is a flow chart illustrating another example method of performing an ablation procedure.

Another example method 900 of performing an ablation treatment is shown in FIG. 9. The method 900 is described below with reference to the ablation system 700 but it should be appreciated that other systems and apparatuses can also be used to perform some or all the steps of method 900.

The method 900 may begin at step 902. At step 902, an ablation probe is positioned at a target tissue in a patient. The probe may be positioned by a medical professional, robotic tool, or other suitable device using image data that may be obtained during or prior to the ablation treatment. The probe that is inserted at the target tissue is a combination probe such as the combination probes of the present disclosure. The combination probe may include an external heater. The combination probe can be operated to perform a cryo ablation cycle and a thermal ablation cycle.

The method 800 then may proceed to step 904. At step 904, the computing device 710 and/or control 708 may determine whether a cooling or thermal cycle is desired. A medical professional may indicate which cycle to perform using an input device to the computing device 710, in some examples. In other examples, the treatment plan may indicate a quantity and order of thermal and cryo cycles that are to be performed during an ablation treatment. The computing device 710 may obtain the treatment plan and then perform the ablation treatment accordingly. If a cryo cycle is desired the method 900 may proceed to step 906. If a thermal cycle is desired, the method 900 may proceed to step 910.

At step 906, the computing device 710 and/or the control 708 may cause the ablation probe to be cooled. This may be performed by the control 708 that may send signals to the pump 714, the valve 718, and/or the cryo-fluid source 716 to cause the cryo-fluid to flow to the probe 702. The cryo-fluid may be circulated through the probe 702 to cause the ice ball 704 to be formed at the target tissue.

At step 908, the ablation conditions of the cryo cycle may be monitored the computing device 710 and/or the control 708 may receive measurement data from the probe, measurement contacts, or other sensors as previously described. While not shown, the operating condition of the system 700 may be adjusted, adapted or otherwise controlled during the cryo cycle to maintain the ablation conditions in a predetermined range or to reach a predetermined threshold. Once these ablation conditions are achieved, the method 900 may proceed to step 914.

At step 914, the computing device 710 and/or the control 708 may determine whether further treatment is needed. The computing device may determine, for example, that another cryo cycle is needed. In other examples, the computing device 710 may determine that a thermal cycle is needed. If further treatment is needed, the method 900 can return to step 904 and re-perform the steps of method 900.

If a thermal cycle is desired, the method 900 moves to step 910. At step 910, the probe is heated. The computing device 710 and/or the control 708 may cause the power supply 720 to supply a power signal to the external heater of the probe 702. This may cause the probe 702 to heat at its location. The thermal cycle may be used to perform a thaw cycle (i.e., to remove the probe from the ice ball), to perform a coagulation cycle if a bleeding condition is detected, to perform a cautery cycle if the probe is to be moved or removed from the ablation site, or to perform an ablation cycle to destroy a target tissue. The control 708 can change, adapt, and/or control the power that is delivered to the external heater of the probe to achieve a desired temperature that may be needed depending on the type of thermal cycle that is desired.

At step 912, the computing device 710 and/or the control 708 may monitor the ablation conditions. The computing device 710 and/or the control 708 may receive measurement data and/or other information as previously described. While the thermal cycle is being performed, the computing device 710 and/or the control 708 may adjust, change, or control the operating conditions of the system 700 to achieve desired conditions for the thermal cycle.

At step 914, the computing device 710 and/or the control 708 may determine whether further treatment is needed. The method 900 may return to step 904 to re-perform thermal or cryo cycles as may be desired. If further treatment is not required, the method 900 may end.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An ablation probe comprising:

a shell comprising:

a main body portion having a main body portion diameter along a length of the main body portion; and a tip portion disposed at a distal end of the shell, the tip portion having a varying tip diameter along an entire length of the tip portion and tapering to a point, wherein the shell is configured to be positioned at a target tissue in a patient;

a conduit positioned inside the shell, the conduit configured to supply a cryo-fluid toward the tip portion of the shell; and a heater disposed around the main body portion of the shell and around the tip portion of the shell, the heater configured to heat the ablation probe to perform thermal ablation.

2. The ablation probe of claim 1, wherein the heater is embedded in a layer of coating positioned on an external surface of the shell.

3. The ablation probe of claim 2, wherein the layer of coating comprises a thermally conductive material.

4. The ablation probe of claim 3, wherein the layer of coating comprises a thermally conductive heat shrink material.

5. The ablation probe of claim 2, wherein the heater comprises a resistive heating wire wrapped around the conduit.

6. The ablation probe of claim 5, wherein the heater is coupled to a power line configured to supply a power signal to the heater, the power line positioned externally to the shell.

7. The ablation probe of claim 6, wherein the layer of coating is positioned over the power line externally to the shell.

8. The ablation probe of claim 2, comprising two or more measurement contacts on an external surface of the ablation probe.

9. The ablation probe of claim 8, wherein the two or more measurement contacts are positioned in the layer of coating.

10. The ablation probe of claim 9, wherein the two or more measurement contacts are configured to collect measurement data regarding operating conditions of the ablation probe.

11. The ablation probe of claim 10, wherein the heater comprises a coil of resistive heating wire and each of the two or more measurement contacts are positioned between adjacent wraps of the coil of resistive heating wire.

12. The ablation probe of claim 11, wherein the two or more measurement contacts comprise an array of measurement contacts positioned around a circumference of the external surface of the ablation probe.

13. The ablation probe of claim 1, wherein the conduit includes at least one opening at or near the tip portion to allow cryo-fluid to exit an interior of the conduit and flow in a return direction between an outer surface of the conduit and an inner surface of the shell.

14. The ablation probe of claim 1, wherein:

the main body portion has a tube shape; and the shell forms an inner cavity in which the conduit is positioned.

15. An ablation probe comprising:

an inner conduit extending axially along an axis;

an outer shell positioned radially outward of the inner conduit, the outer shell comprising:

a main body portion extending along the axis and having a main body portion diameter along a length of the main body portion; and a tip portion disposed at a distal end of the outer shell, the tip portion having a varying tip diameter along an entire length of the tip portion and tapering to a point;

a coil of resistive wire positioned externally to the outer shell around the main body portion of the outer shell, and around the tip portion of the outer shell, the coil configured to heat the ablation probe to a predetermined temperature sufficient to perform thermal ablation; and a layer of coating positioned around the coil of resistive wire separating the coil of resistive wire from an external surface of the ablation probe.

16. A method of performing an ablation treatment comprising:

positioning the ablation probe of claim 1 at or near the target tissue in the patient;

cooling the ablation probe using the cryo-fluid circulated through the ablation probe to cause an ice ball to be formed at the target tissue; and heating the ablation probe using the heater.

17. The method of claim 16, wherein the step of heating the ablation probe comprises heating the ablation probe to a temperature greater than or equal to 150° C.

18. The method of claim 16, wherein the ablation probe remains in a predetermined position at or near the target tissue during the step of cooling the ablation probe and the step of heating the ablation probe.

19. The method of claim 16, further comprising obtaining measurement data from two or more measurement contacts.

* * * * *